US010526612B2

(12) United States Patent
Numata et al.

(10) Patent No.: US 10,526,612 B2
(45) Date of Patent: *Jan. 7, 2020

(54) PLANT TRANSFORMATION METHOD

(71) Applicant: Riken, Wako-shi, Saitama (JP)

(72) Inventors: Keiji Numata, Wako (JP); Takeshi Yoshizumi, Tsuruoka (JP); Yutaka Kodama, Utsunomiya (JP)

(73) Assignee: Riken, Saitama (JP)

( * ) Notice: Subject to any disclaimer, the term of this patent is extended or adjusted under 35 U.S.C. 154(b) by 50 days.

This patent is subject to a terminal disclaimer.

(21) Appl. No.: 15/123,139

(22) PCT Filed: Mar. 5, 2015

(86) PCT No.: PCT/JP2015/057221
§ 371 (c)(1),
(2) Date: Sep. 1, 2016

(87) PCT Pub. No.: WO2015/133652
PCT Pub. Date: Sep. 11, 2015

(65) Prior Publication Data
US 2017/0058283 A1 Mar. 2, 2017

(30) Foreign Application Priority Data
Mar. 6, 2014 (JP) .................. 2014-044046

(51) Int. Cl.
*C12N 15/82* (2006.01)
(52) U.S. Cl.
CPC ..... *C12N 15/8206* (2013.01); *C12N 15/8201* (2013.01)
(58) Field of Classification Search
None
See application file for complete search history.

(56) References Cited

U.S. PATENT DOCUMENTS

| | | | |
|---|---|---|---|
| 5,036,006 A | 7/1991 | Sanford et al. | |
| 5,736,369 A | 4/1998 | Bowen et al. | |
| 2006/0014712 A1* | 1/2006 | Neuman ............ | A61K 38/1709 514/44 A |
| 2011/0035836 A1* | 2/2011 | Eudes ................ | C12N 15/8206 800/278 |
| 2011/0247100 A1 | 10/2011 | Samboju et al. | |
| 2015/0218569 A1 | 8/2015 | Numata et al. | |
| 2015/0344897 A1 | 12/2015 | Wang et al. | |

FOREIGN PATENT DOCUMENTS

| | | |
|---|---|---|
| EP | 0665290 | 8/1995 |
| JP | 7-213285 | 8/1995 |
| JP | 10-503374 | 3/1998 |
| JP | 2013-507919 | 3/2013 |
| JP | 2013-523121 | 6/2013 |
| WO | 9604392 | 2/1996 |
| WO | 00/56904 | 9/2000 |
| WO | 2011006133 | 1/2011 |
| WO | 2011/017808 | 2/2011 |
| WO | 2011/046786 | 4/2011 |
| WO | 2011/126644 | 10/2011 |
| WO | 2013129698 | 9/2013 |
| WO | 2014/006452 | 1/2014 |
| WO | 2014/029044 | 2/2014 |

OTHER PUBLICATIONS

Eudes et al 2008 (Cell-penetrating peptides. Plant Signaling & Behavior. 3:8, 549-550; 2008).*
Zimmerman et al (Genetic transformation through the use of hyperhydric tobacco Meristems. Molecular Breeding 20: 73-80, 1996).*
Eggenberger et al (Using the Peptide Bp100 as a Cell-Penetrating Tool for the Chemical Engineering of Actin Filaments within Living Plant Cells. ChemBioChem 12:132-137, 2011).*
Ishihara et al (Intracellular delivery of siRNA by cell-penetrating peptides modified with cationic oligopeptides. Drug Delivery, 16(3): 153-159, 2009). (Year: 2009).*
Lakshmanan, Manoj, et al., "Rapid and Efficient Gene Delivery into Plant Cells Using Designed Peptide Carriers", Biomacromolecules, Jan. 14, 2013, vol. 14, No. 1, pp. 10-16.
Chugh, Archana, et al., "Cell-Penetrating Peptides: Nanocarrier for Macromolecule Delivery in Living Cells", IUBMB Life, Mar. 25, 2010, vol. 62, No. 3, pp. 183-193.
Supplementary European Search Report, dated Sep. 21, 2017 based on co-pending European Patent Application No. 15758536.5, 9 Pages.
Lowe, Keith, et al., "Germline Transformation of Maize Following Manipulation of Chimeric Shoot Meristems", Biotechnology, Jul. 1995, vol. 13, pp. 677-682.
International Search Report based on International Application No. PCT/JP2015/057221, dated Jun. 9, 2015.
European Office Action dated Feb. 11, 2019, pertaining to co-pending European Patent Application No. 15758536.5—5 Pages.
Japanese Office Action dated Mar. 12, 2019, pertaining to co-pending Japanese Patent Application No. 2016-506214—5 Pages.

* cited by examiner

*Primary Examiner* — Medina A Ibrahim
*Assistant Examiner* — Wayne Zhong
(74) *Attorney, Agent, or Firm* — McCarter & English, LLP

(57) ABSTRACT

An object of the present invention is to provide a plant transformation method that is convenient and is widely applicable to various types of plant cells and nucleic acids. The present invention relates to a method for transforming a target plant, comprising the steps of: a) contacting a carrier peptide comprising a cell-penetrating sequence and a polycation sequence with a nucleic acid to form a complex; b) contacting the obtained complex with a cell of a meristem of the target plant to transfer the nucleic acid to the genome; c) allowing the meristem to grow; and d) selecting a plant harboring the transferred nucleic acid.

10 Claims, 7 Drawing Sheets
Specification includes a Sequence Listing.

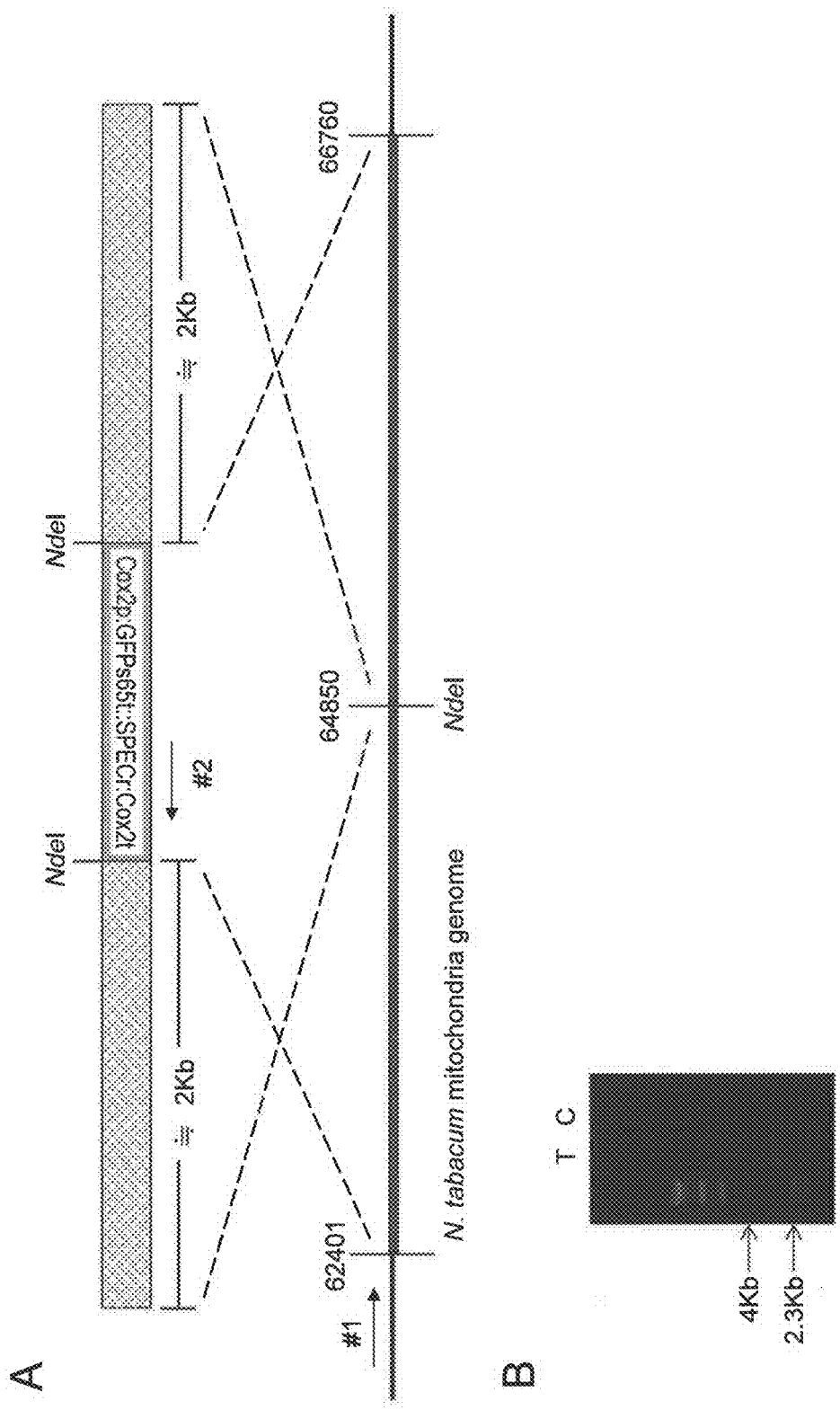

PLANT TRANSFORMATION METHOD

RELATED APPLICATIONS

This application is a national stage application filed under 35 USC 371 of PCT/JP2015/057221, filed Mar. 5, 2015, which claims the benefit of Japanese Patent Application No. 2014-044046, filed Mar. 6, 2014, all of which are incorporated herein, in entirety, by reference.

The Sequence Listing associated with this application is filed in electronic format via EFS-Web and hereby incorporated by reference into the specification in its entirety. The name of the text file containing the Sequence Listing is 119244_00096 Revised_Sequence_Listing. The size of the text file is 18 KB, and the text file was created on Aug. 28, 2019.

TECHNICAL FIELD

The present invention relates to a method for transforming a plant by transferring a nucleic acid to the genome of the plant using a carrier peptide comprising a plurality of functional domains.

BACKGROUND ART

For future improvement in agricultural crops and agricultural development, it is very important to impart useful properties, which cannot be imparted by hybridization breeding, to plants by transferring foreign genes to the plant cells. Also, the exploitation of a gene recombination technique of plants is indispensable for achieving matter production using plants with carbon dioxide as a raw material, as a novel matter production method that substitutes for petroleum-dependent matter production.

However, a plant transformation method has been established for model plants for use in general research, but has not yet been established or is very difficult to be carried out for many crops. Various gene transfer methods for plant cells such as Agrobacterium method, particle gun method, and whisker method have been developed. The act of sending a gene into cells is theoretically possible in itself for any plant. The reason why the transformation method has not yet been established for many plants is that, for example, a tissue culture method has not been established. In a general transformation method, undifferentiated cells such as callus are prepared from a plant tissue, and a foreign gene is transferred thereto using Agrobacterium or a particle gun. Since the foreign gene contains a selective marker gene such as an antibiotic resistance gene, cells harboring the transferred gene are selected by growing the cells on a medium containing the antibiotic after the gene transfer. Then, the selected cells are allowed to grow on a medium containing various concentrations of plant hormones for redifferentiation (rooting and shoot formation) to prepare a transformed individual. However, an approach for this tissue culture has not been established for many crops. Therefore, it has been difficult to obtain a transformed individual even if a gene has been transferred to the plants.

The in planta transformation method is a method which involves directly transferring a gene to an untreated plant individual or tissue and obtaining a transformed individual by a method that utilizes the life cycle of the plant. This method does not require tissue culture and is therefore applicable to even crops for which the transformation method has not yet been established. In the case of this method, the target cells for gene transfer are cells that produce progeny, i.e., cells of shoot apical meristems, pollens, and ovules. Examples of the in planta transformation most used include the DIP infiltration method of *Arabidopsis thaliana*. This method is a very convenient method which involves transferring a gene to, mainly, the ovule by dipping a flower of *Arabidopsis thaliana* in a culture solution of *Agrobacterium*, and pollinating this ovule to obtain transformed seeds. However, because of the difficulty in procedures of dipping a flower of the plant in a culture solution of *Agrobacterium*, this method is limited to *Arabidopsis thaliana*. Thus, the conventional gene transfer methods are difficult to be exploited in the in planta transformation, because the methods are limited by subject plants, tissue sizes, etc.

A cell-penetrating peptide (CPP) is known to have the function of transporting a complex comprising the peptide and another substance (e.g., a protein or a nucleic acid) through biomembranes in mammalian and human cell lines. However, the use of CPP is limited to plant cells. This is because, unlike animal cells, plant cells have a double bottleneck, i.e., a cell wall and a cell membrane, against the internalization of the complex comprising CPP. It has been found that a polycationic peptide concentrates negatively charged DNA through ionic interaction and forms a complex available for gene delivery, and the complex is useful in gene transfer to animal cells (Patent Literature 1). Also, a case using the polycationic peptide in gene transfer to a plant protoplast has been reported (Patent Literature 2). However, this method employs a cell wall-free protoplast and is not satisfactory in terms of gene transfer efficiency for plant cells.

CITATION LIST

Patent Literature

Patent Literature 1: WO2011/006133
Patent Literature 2: JP Patent Publication (Kokai) No. 7-213285 A (1995)

SUMMARY OF INVENTION

An object of the present invention is to provide a plant transformation method that is convenient, is widely applicable to various types of plants and nucleic acids, and does not require tissue culture.

The present inventors have found that a transformant is obtained, without the need of tissue culture, by constructing a carrier peptide as a fusion peptide of a cell-penetrating sequence combined with a polycation sequence, mixing the carrier peptide with a nucleic acid to form a complex, and applying the complex to a meristem of a plant to transfer the nucleic acid to the genome of the plant. On the basis of this finding, the present invention has been completed.

Specifically, the present invention encompasses the following aspects.

(1) A method for transforming a target plant, comprising the steps of:
a) contacting a carrier peptide comprising a cell-penetrating sequence and a polycation sequence with a nucleic acid to form a complex;
b) contacting the obtained complex with a cell of a meristem of the target plant to transfer the nucleic acid to the genome;
c) allowing the meristem to grow; and
d) selecting a plant harboring the transferred nucleic acid.

(2) The method according to (1), wherein the cell-penetrating sequence is BP100.

(3) The method according to (1) or (2), wherein the polycation sequence comprises at least three amino acid residues selected from lysine (K), arginine (R), and histidine (H).

(4) The method according to (3), wherein the polycation sequence comprises a sequence of 3 to 20 KH repeats (SEQ ID NO: 42).

(5) The method according to any of (1) to (4), wherein the nucleic acid comprises a marker gene.

(6) The method according to any of (1) to (5), wherein the plant is a seed plant, wherein the method further comprises the step of allowing the plant selected in the step d) to grow to collect a seed.

(7) The method according to any of (1) to (6), wherein the meristem is a shoot apical meristem.

(8) A method for transferring a nucleic acid to the genome of a target plant, comprising the steps of:
a) contacting a carrier peptide comprising a cell-penetrating sequence and a polycation sequence with the nucleic acid to form a complex; and
b) contacting the obtained complex with a cell of a meristem of the target plant to transfer the nucleic acid to the genome.

(9) The method according to (8), wherein the cell-penetrating sequence is BP100.

(10) The method according to (8) or (9), wherein the polycation sequence comprises at least three amino acid residues selected from lysine (K), arginine (R), and histidine (H).

(11) The method according to (10), wherein the polycation sequence comprises a sequence of 3 to 20 KH repeats (SEQ ID NO: 42).

(12) The method according to any of (8) to (11), wherein the meristem is a shoot apical meristem.

(13) A method for producing a plant transformant using the method according to any of (1) to (12).

(14) A plant transformant obtained by the method according to (13).

The present invention provides a plant transformation method that is convenient, is widely applicable to various types of plant cells and nucleic acids, and does not require tissue culture.

The present specification encompasses the contents described in the specification and/or drawings of Japanese Patent Application No. 2014-044046 to which the present application claims priority.

BRIEF DESCRIPTION OF DRAWINGS

FIG. 4-1 is a schematic diagram showing one embodiment of a transformation method of directly transferring a solution of a complex of a carrier peptide and a nucleic acid to a target plant. FIG. 4-1A is a schematic diagram showing that the solution of the complex is added dropwise to cells of a meristem of the target plant using a dropper or the like, FIG. 4-1B is an enlarged photograph of the meristem of the target plant to which the solution of the complex is added dropwise. The solution of the complex was added dropwise to a shoot apical meristem represented by b in the diagram. FIG. 4-1C is a schematic diagram showing the neighborhood of the shoot apical meristem of the plant. In the diagram, a represents the leaf primordium, b represents the shoot apical meristem, c represents the L3 layer, d represents the L1 and L2 layers, e represents the central zone, f represents the rib zone, g represents the peripheral zone, h represents the L1 layer, and i represents the L2 layer.

FIG. 4-2 is a schematic diagram showing another embodiment of a transformation method of directly transferring a solution of a complex of a carrier peptide and a nucleic acid to a target plant, as in FIG. 4-1. FIG. 4-2A is a schematic diagram showing that the solution of the complex is injected to cells of a meristem of the target plant using a syringe or the like. FIG. 4-2B is an enlarged photograph of the meristem of the target plant to which the solution of the complex is injected. The solution of the complex was injected to an area within the white box (shoot apical meristem) in the diagram. FIG. 4-2C is the same as FIG. 4-1C.

FIG. 5 is a diagram showing the transfer of a foreign nucleic acid of interest to the *Nicotiana tabacum* mitochondrial genome by the transformation method of the present invention. FIG. 5A is a schematic diagram showing the transfer of the foreign nucleic acid of interest to *Nicotiana tabacum* mitochondrial genomic DNA. FIG. 5B shows agarose gel electrophoretograms of PCT products for a transformant (T) and a control (C).

FIG. 6A is a schematic diagram showing the transfer of the foreign nucleic acid of interest to *Arabidopsis thaliana* chloroplast genomic DNA. FIG. 6B shows agarose gel electrophoretograms of PCT products for a transformant (T) and a control (C). FIG. 6C is a photograph showing fluorescence from the chloroplast in the transformant.

DESCRIPTION OF EMBODIMENTS

Figure 1:
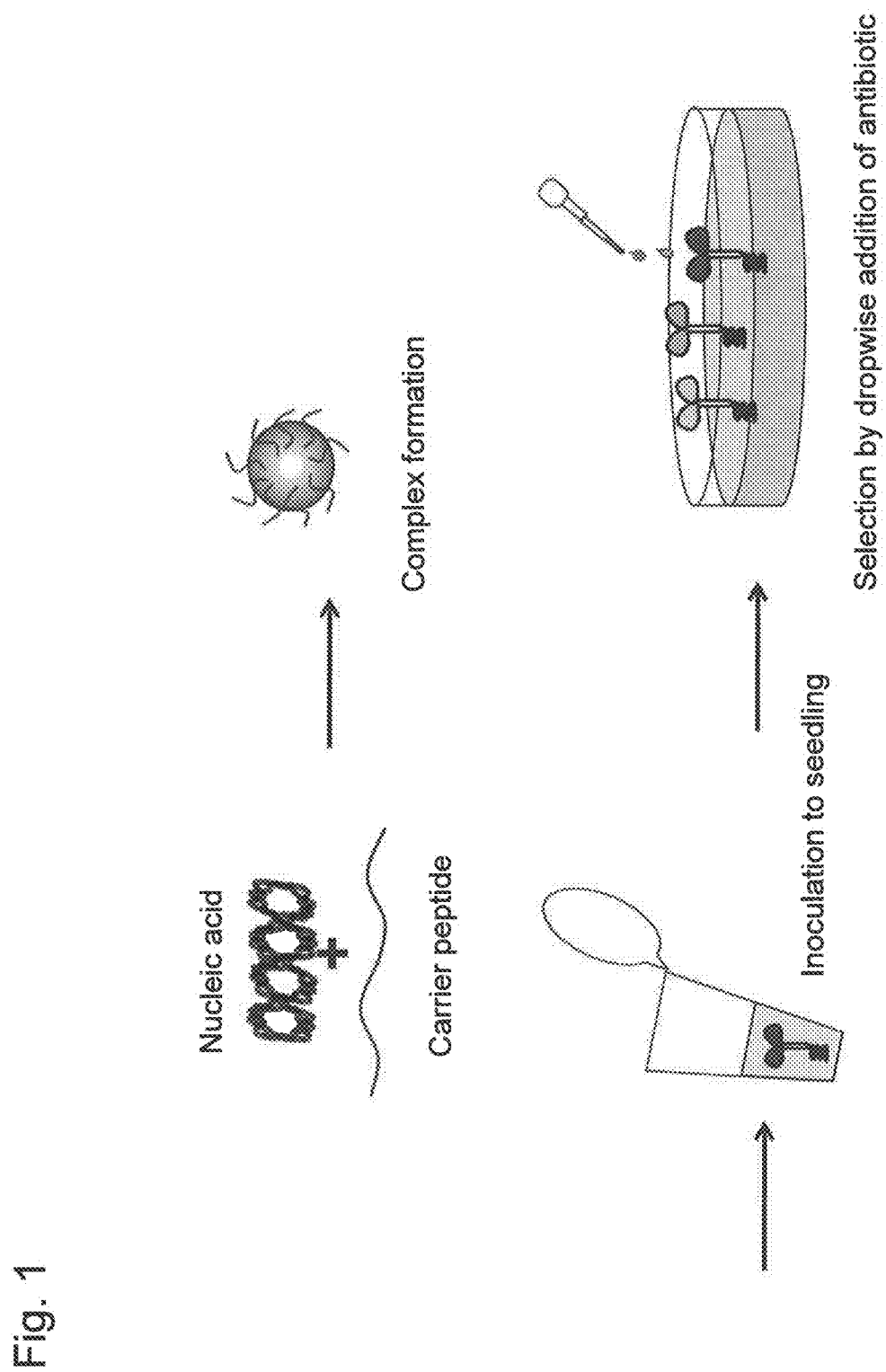
FIG. 1 is a schematic diagram showing one embodiment of a complex of a carrier peptide and a nucleic acid and a plant transformation method using the complex.

The present invention relates to a method for transforming a target plant, comprising the steps of: a) contacting a carrier peptide comprising a cell-penetrating sequence and a polycation sequence with a nucleic acid to form a complex; b) contacting the obtained complex with a cell of a meristem of the target plant to transfer the nucleic acid to the genome; c) allowing the meristem to grow; and d) selecting a plant harboring the transferred nucleic acid.

In the present invention, the nucleic acid to be transferred to the genome of the plant is usually DNA which may be linear or may be circular. Also, the DNA may be single-stranded or may be double-stranded. The DNA encompasses DNA molecules of every type and size, for example, DNA including cDNA, plasmids, genomic DNA, and their derivatives. In addition, such a nucleic acid may be chemically modified as long as the negative charge of a phosphate backbone that mediates the ionic bond to the polycation sequence of the carrier peptide is preserved. Examples of the suitably modified nucleic acid can include thioate and dithioate. In this respect, other suitable nucleic acid derivatives are mentioned in, for example, Uhlnmann & Peymann, Chemical Reviews, 90 (4), 544-584, 1990.

Furthermore, a nucleic acid having a chemically modified nucleotide base may be used. The nucleic acid to be transferred to the genome of the cell of the target plant is preferably modified DNA, if desired. For example, the nucleic acid to be transferred to the cell of the target plant may include genetic information that is to be expressed in the cell of the target plant. For example, a gene-dependent defect can be removed by this method.

The transformation method of the present invention is characterized by that the method can transfer the nucleic acid to the genome of the plant cell without being limited by the type or size of the nucleic acid. In the case of, for example, double-stranded DNA, the size of the nucleic acid to be transferred is on the order of usually 20 base pairs to 20 kilo base pairs, preferably 50 base pairs to 10 kilo base pairs.

In the present specification, the transfer of a nucleic acid to a plant cell is described. However, the present invention can be applied to any cells having a cell membrane, including animal cells. In the present invention, the plant cell means a cell other than animal cells and in other words, a cell having a cell wall. The type of the plant cell is not particularly limited, and the present invention can be applied to every plant cell such as angiosperms (including monocotyledons and dicotyledons) and gymnosperms (seed plants), bryophytes, pteridophytes, herbaceous plants, and woody plants. Specific examples of the plant include plants of the family Solanaceae [*Solanum melongena* L., *Solanum lycopersicum, Capsicum annuum* L. var. *angulosum* Mill., *Capsicum annuum* L., *Nicotiana tabacum* L., etc.], the family Poaceae [*Oryza sativa, Trilicum aestivum* L., *Hordeum vulgare* L., *Lolium perenne* L., *Lolium multiflorum* Lam., *Festuca pratensis* Huds., *Festuca arundinacea* Schreb., *Dactylis glomerata* L., *Phleum pratense* L., etc.], the family Brassicaceae [*Arabidopsis thaliana, Brassica campestris* L., *Brassica pekinensis* Rupr., *Brassica oleracea* L. var. *capitala* L., *Raphanus sativus* L., *Brassica campestris* L., *B. napus* L., etc.], the family Leguminosae [*Glycine max, Vigna angularis* Willd., *Phaseolus vulgaris* L., *Vicia faba* L., etc.], the family Cucurbitaceae [*Cucumis sativus* L., *Cucumis melo* L., *Citrullus vulgaris* Schrad., *C. moschata* Duch., *C. maxima* Duch., etc.], the family Convolvulaceae [*Ipomoea batatas*, etc.], the family Liliaceae [*Allium fistulosum* L., *Allium cepa* L., *Allium tuberosum* Rottl., *Allium sativum* L., *Asparagus officinalis* L., etc.], the family Lamiaceae [*Perilla frulescens* Britt. var. *crispa*, etc.], the family Compositae [*Chrysanthemum morifolium, Chrysanthemum coronarium* L., *Lactuca sativa* L. var. *capitata* L., etc.], the family Rosaceae [*Rose hybrida* Hort., *Fragaria x ananassa* Duch., etc.], the family Rutaceae [*Citrus unshiu, Zanthoxylum piperitum* DC., etc.], the family Myrtaceae [*Eucalyptus globulus* Labill, etc.], the family Saliaceae [*Populus nigra* L. var. *italica* Koehne, etc.], the family Chenopodiaceae [*Spinacia oleracea* L., *Beta vulgaris* L., etc.], the family Gentianaceae [*Gentiana scabra* Bunge var. *buergeri* Marim., etc.], and the family Caryophyllaceae [*Dianthus caryophyllus* L., etc.]. Among them, a plant of the family Solanaceae, particularly, *Nicotiana tabacum* L., is preferably used.

The present invention is characterized by that the nucleic acid is transferred to the genome of the cell of the plant meristem using the carrier peptide. Specifically, a peptide-nucleic acid complex is contacted with the cell of the plant meristem to transfer the nucleic acid to the genome of the cell of the plant meristem. In the present invention, the genome encompasses nuclear genome, mitochondrial genome, and chloroplast genome. As a result of transferring the nucleic acid to the genome of the cell of the meristem, tissues of roots, leaves, flowers, and the like yielded after the nucleic acid transfer are all constituted by transformed cells.

The meristem refers to a tissue that is composed of undifferentiated cells in a plant and is under active cell division. In other words, the cell of the plant meristem encompasses undifferentiated cells and cells under active cell division in plants. Specifically, the plant meristem encompasses apical meristems, secondary meristems, and lateral meristems. The apical meristems are tissues that are found in the growth points of shoot apices and root tips and related to growth and differentiation in the longitudinal direction. The secondary meristems and the lateral meristems are tissues of the cambium or the like that are related to growth in the horizontal direction (thickening of stems, etc.). The apical meristems encompass shoot apical meristems which serve as growth points for stems, and root tip ineristems which serve as growth points for roots. The cell of the meristem encompasses fusiform initial cells and ray initial cells contained in the cambium.

In the present invention, it is particularly preferred to contact the peptide-nucleic acid complex with the cell of the shoot apical meristem to transfer the nucleic acid to the genome. Plants form leaves or flowers depending on the environments where they grow. All of such organs of the above-ground parts are formed from the shoot apical meristems. Therefore, leaves or flowers yielded after the nucleic acid transfer are all constituted by transformed cells when transferring the nucleic acid to the shoot apical meristem and inserting it into the genome. Then, progeny seeds thereof are also transformants. Thus, the method of the present invention has the advantages that the method does not require tissue culture and further, for example, somatic mutation, which often occurs during tissue culture, is absent in the method. For cells for which a tissue culture method has been established, the cells after the nucleic acid transfer may be cultured to obtain transformed individual(s).

The carrier peptide used in the present invention is a peptide that can form a peptide-nucleic acid complex through ionic interaction with the nucleic acid and function as a carrier facilitating nucleic acid transfer to the genome of the plant cell. The carrier peptide is characterized by comprising a cell-penetrating sequence and a polycation sequence. In the present invention, the peptide may contain a sugar chain, a lipid, and/or a phosphate residue, in addition to the peptide component.

The cell-penetrating sequence means the sequence of a cell-penetrating peptide (CPP). Examples of the cell-penetrating peptide include, but are not limited to, BP100 (Appl Environ Microbiol 72 (5), 3302, 2006), HIV Tat (Journal Biological Chemistry, 272, pp. 16010-16017, 1997), $Tat_2$ (Biochim Biophys Acta 1768 (3), 419, 2007), Penetratin, pVEC, pAntp (Journal Biological Chemistry, 269, pp. 10444-10450, 1994), HSV-1 VP22 (Cell, 88, pp. 223-233, 1997), MAP (model amphiphilic peptide) (Biochimica Biophysica Acta, 1414, pp. 127-139, 1998), Transportan (FEBS Journal, 12, pp. 67-77, 1998), R7 (SEQ ID NO: 44) (Nature Medicine, 6, pp. 1253-1257, 2000), MPG (Nucleic Acid Research 25, pp. 2730-2736, 1997), and Pep-1 (Nature Biotechnology, 19, pp. 1173-1176, 2001). A peptide sequence, in which one to several amino acid residues in any of these peptide sequences are substituted, inserted, and/or deleted, may be suitably used. Two or more cell-penetrating peptides may be used in combination as the cell-penetrating peptide. The carrier peptide may comprise two or more cell-penetrating sequences. It is also preferred to select a cell-penetrating peptide specific for the particular cell of interest.

Specific examples of the cell-penetrating sequence can include the following sequences: KKLFKKILKYL (SEQ ID NO: 1), RKKRRQRRRRKKRRQRRRR (SEQ ID NO: 2), RKKRRQRRR (SEQ ID NO: 3), PLSSIFSRIGDP (SEQ ID NO: 4), PISSIFSRTGDP (SEQ ID NO: 5), AISSILSKTGDP (SEQ ID NO: 6), PILSIFSKIGDL (SEQ ID NO: 7), PLSSIFSKIGDP (SEQ ID NO: 8), PLSSIFSHIGDP (SEQ ID NO: 9), PLSSIFSSIGDP (SEQ ID NO: 10), RQIKIW-FQNRRMKWKK (SEQ ID NO: 11), DAATATRGRSAAS-RPTERPRAPARSASRPRRPVD (SEQ ID NO: 12), AAVALLPAVLLALLAP (SEQ ID NO: 13), AAVLLPVL-LAAP (SEQ ID NO: 14), VTVLALGALAGVGVG (SEQ ID NO: 15), GALFLGWLGAAGSTMGA (SEQ ID NO: 16), MGLGLHLLVLAAALQGA (SEQ ID NO: 17), LGTYTQDFNKFHTFPQTAIGVGAP (SEQ ID NO: 18), GWTLNSAGYLLKINLKALAALAKKIL (SEQ ID NO: 19), and KLALKLALKALKAALKLA (SEQ ID NO: 20).

The polycation sequence is a peptide sequence that comprises at least three amino acid residues selected from lysine (K), arginine (R), and histidine (H) and forms a stable bond with the nucleic acid under physiological conditions. In addition to the positively charged amino acid residues (cationic amino acid residues), i.e. lysine, arginine, and histidine, the polycation component can also include a neutral amino acid provided that the resulting sequence maintains its adequate cationic properties as a whole and forms a stable bond with the nucleic acid under physiological conditions. This can be tested by a simple experiment which involves adding the nucleic acid. For example, a peptide that forms such a stable peptide-nucleic acid complex that a delay of the nucleic acid band occurs in agarose gel electrophoresis is suitable. This delay of the nucleic acid band indicates that the peptide-nucleic acid complex is retained throughout the agarose gel electrophoresis.

The polycation sequence in the carrier peptide must comprise at least three lysine, arginine, and/or histidine residues, though the upper limit cannot be defined. It is known that the polycation sequence can comprise 450 amino acid residues at the maximum and is still functional in this state (Proc Natl Acad Sci USA 87, 3410-3414, 1990). However, the length of the polycation sequence is preferably 5 to 100 amino acid residues, more preferably 5 to 50, further preferably 7 to 20 amino acid residues. The proportion of the cationic amino acid residues in the polycation sequence is preferably 40% by mol or more, more preferably 60% by mol or more, further preferably 80% by mol or more, most preferably 90% by mol or more. A polycation sequence consisting of only the polycationic amino acid residues is most preferably used.

The polycation sequence comprises preferably 4 or more, more preferably 5 or more, further preferably 7 or more and preferably 30 or less, more preferably 25 or less, further preferably 20 or less lysine, arginine and/or histidine residues. Furthermore, the polycation sequence preferably has a series of 3 or more consecutive lysine, arginine, and/or histidine residues, more preferably has a series of 5 or more consecutive lysine, arginine, and/or histidine residues, particularly preferably has a series of 7 or more consecutive lysine, arginine, and/or histidine residues. Among the cationic amino acid residues, a higher proportion of arginine tends to accelerate transfer into the cell, and higher proportions of histidine and lysine tend to slow down transfer into the cell. For example, the transfer rate into the cell can be controlled by appropriately selecting the polycation sequence according to the use purpose of the complex of the present invention, such as organelle-specific transfer described below. Preferred examples of the polycation sequence include KH repeat sequences, for example, a sequence of 3 to 20 KH repeats (SEQ ID NO: 42), more preferably a sequence of 5 to 15 KH repeats (SEQ ID NO: 45), further preferably a sequence of 7 to 12 KH repeats (SEQ ID NO: 46). Examples thereof also include: consecutive sequences of arginine (R), for example, a sequence of 3 to 20 consecutive R residues (SEQ ID NO: 55), preferably a sequence of 5 to 15 consecutive R residues (SEQ ID NO: 47), more preferably a sequence of 7 to 12 consecutive R residues (SEQ ID NO: 48); consecutive sequences of lysine (K), for example, a sequence of 3 to 20 consecutive K residues (SEQ ID NO: 49), preferably a sequence of 5 to 15 consecutive K residues (SEQ ID NO: 50), more preferably a sequence of 7 to 12 consecutive K residues (SEQ ID NO: 51); and consecutive sequences of histidine (H), for example, a sequence of 3 to 20 consecutive H residues (SEQ ID NO: 52), preferably a sequence of 5 to 15 consecutive H residues (SEQ ID NO: 53), more preferably a sequence of 7 to 12 consecutive H residues (SEQ ID NO: 54).

Specific examples of the polycation sequence can include the following sequences: RRRRRR (SEQ ID NO: 21) and KHKHKHKHKHKHKHKHKH (SEQ ID NO: 22).

The carrier peptide comprises a constituent corresponding to a linear fusion of the cell-penetrating sequence and the polycation sequence. For this fusion, it is preferred that the polycation sequence should be bound to the N terminus and/or the C terminus of the cell-penetrating sequence. The cell-penetrating sequence can be bound with one or two or more polycation sequences described above, preferably one to several, more preferably one to approximately three polycation sequences described above. Particularly preferably, the cell-penetrating sequence can be bound with one polycation sequence. The binding may be chemically performed according to usual peptide binding reaction or may be biologically performed using an enzyme such as ligase. For example, the binding can also be performed according to a general peptide synthesis method such as a solid-phase method. In order to bind the cell-penetrating sequence to the polycation sequence, an appropriate oligopeptide linker or the like can also be present between these sequences. For example, a linker composed of one to several amino acids can be present therebetween. The amino acid residues constituting the linker can be appropriately selected. Since the cell-penetrating peptide exhibits its properties via the N terminus, it is preferred that the cell-penetrating sequence should be bound to the N terminus of the polycation sequence. The carrier peptide can also be obtained by a recombinant DNA technique. For example, a DNA fragment encoding the polycation sequence is bound to one end or both ends of a DNA fragment encoding the cell-penetrating sequence through linkage reaction with an appropriate DNA adaptor or in vitro mutagenesis. Such a gene manipulation method is well known to those skilled in the molecular biological field.

The carrier peptide can further comprise an organelle transit sequence in addition to the cell-penetrating sequence and the polycation sequence. The organelle transit sequence refers to the sequence of a peptide having affinity for or permeability to a particular intracellular organelle. It is preferred to use the sequence of a peptide having affinity for or permeability to a mitochondrion or a chloroplast. More specific examples thereof can include, but are not limited to, chloroplast transit peptides originated from chlamydomonas ferredoxin (Cf) and chlamydomonas Rubisco activase (CRa), a mitochondrial matrix targeting signal peptide (Biochemical and Biophysical Research Communications, 226, pp. 561-565, 1996), mitochondrial inner membrane targeting signal peptides SS01, SS02. SS31, and SS20 (The AAPS Journal, 8, pp. E277-E283, 2006), 50S ribosomal protein L28, 50S ribosomal protein 1.24, 50S ribosomal protein L27. RuBisCo small chain, and LHCII type 1.

A peptide sequence, in which one to several amino acid residues in any of these peptide sequences are substituted, inserted, and/or deleted, may be suitably used. One or an appropriate combination of two or more of these sequences can be used.

The formation of the complex by contacting the carrier peptide comprising the cell-penetrating sequence and the polycation sequence with the nucleic acid may be performed in the presence of another carrier peptide comprising an organelle transit sequence. In this case, it is preferred that the carrier peptide comprising an organelle transit sequence should also comprise a polycation sequence. This carrier peptide comprising an organelle transit sequence and a polycation sequence can form a complex with the nucleic acid, together with the carrier peptide comprising the cell-penetrating sequence and the polycation sequence. Although the relative arrangement between the organelle transit sequence and the polycation sequence is not limited, it is preferred that the organelle transit sequence should be bound to the C terminus of the polycation sequence. The carrier peptide comprising an organelle transit sequence and a polycation sequence as well as the carrier peptide comprising an organelle transit sequence, the polycation sequence, and the cell-penetrating sequence can be prepared in the same way as above.

Specific examples of the organelle transit sequence can include the following sequences: MAMAMRSTFAARV-GAKPAVRGARPASRMSCMA (SEQ ID NO: 23), MQVT-MKSSAVSGQRVGGARVATRSVRRAQLQV (SEQ ID NO: 24), MATMVAGISLRGPVMSSHRTFSVTKRASL-PQSKLSSELSFVTSQLSGLKISSTHIFISSSA PLSVP-FKPSLQPVA (SEQ ID NO: 25), MAALQSSFAGLSTSFF-GQRFSPPLSLPPLVKSTEGPCLIQA (SEQ ID NO: 26), MAVSFSLVGAFKGLSLASSSSFLKGDFGAAFPVAP-KFSVSFPLKSPLTIES (SEQ ID NO: 27), MASSV-LSSAAVATRSNVAQANMVAQANMVAPTGLKSAASF-PVSRKQNLDISIASNGGRVQC (SEQ ID NO: 28), MAASTMALSSPAFAGKAVKLSPAASEVLGSCRVTM-RKTV (SEQ ID NO: 29), MLSLRQSIRFFK (SEQ ID NO: 31), and MAMQAMFAFQYLLVM (SEQ ID NO: 32).

By use of the carrier peptide comprising the organelle transit sequence, the nucleic acid transferred to the plant cell can be further transferred specifically to the intracellular organelle. It is known that the mitochondrial genome or the chloroplast genome has several tens or several thousands of copies, as compared with the nuclear genome, and permits large-scale production of a foreign protein through its transformation. Therefore, bio-substances that substitute for petroleum resources, or other useful substances can be produced at a large scale by specifically transferring the nucleic acid to the intracellular organelle to optimize the matter production function of the plant.

The carrier peptide comprising an organelle transit sequence and a polycation sequence forms a complex with the nucleic acid, together with the carrier peptide comprising the cell-penetrating sequence and the polycation sequence so that the nucleic acid can be effectively transferred specifically to the intracellular organelle. However, even without the carrier peptide comprising the cell-penetrating sequence and the polycation sequence, i.e. the carrier peptide comprising an organelle transit sequence and a polycation sequence alone forms a complex with the nucleic acid so that the nucleic acid can be transferred specifically to the intracellular organelle.

In the step of contacting the carrier peptide with the nucleic acid to form a complex, it is preferred that the contact should be performed such that the number of an amine group derived from the carrier peptide/the number of a phosphate group derived from the nucleic acid (N/P ratio) is 2 or less. It is also preferred that the contact should be performed such that the N/P ratio is larger than 0.1. The N/P ratio is more preferably 0.2 or more, further preferably 0.3 or more, particularly preferably 0.4 or more. The N/P ratio is also more preferably 1.5 or less, further preferably 1.0 or less, particularly preferably 0.6 or less. A complex formed at a N/P ratio of 0.5 is most preferred. High transfection efficiency for plant cells can be achieved by forming a complex through the contact between the carrier peptide and the nucleic acid at such a N/P ratio (WO2013/129698). In the case of contacting the carrier peptide comprising an organelle transit sequence with the nucleic acid, aside from the carrier peptide comprising the cell-penetrating sequence and the polycation sequence, the number of amine groups derived from all of the carrier peptides serves as a basis.

The step of contacting the carrier peptide with the nucleic acid to form a complex can be carried out, for example, by mixing the carrier peptide and the nucleic acid in a solution. In this case, the concentration of the carrier peptide is usually 10 µg/mL to 10 mg/mL, preferably 100 µg/mL to 1 mg/mL, and the concentration of the nucleic acid in the solution is usually 1 µg/ml, to 10 mg/mL, preferably 10 µg/mL to 1 mg/mL.

The complex of the carrier peptide and the nucleic acid thus formed is obtained by contacting the carrier peptide with the nucleic acid and is not limited by its binding pattern and form. The complex of the carrier peptide and the nucleic acid is usually in the form of a particle, and its average hydrodynamic diameter is preferably 150 nm or larger, more preferably 200 nm or larger, further preferably 300 nm or larger and is also preferably 500 nm or smaller, more preferably 400 nm or smaller, further preferably 350 nm or smaller. The average hydrodynamic diameter can be measured by a dynamic light scattering (DLS) method. High transfection efficiency for plant cells can be achieved by the complex having such an average hydrodynamic diameter (WO2013/129698).

Figure 2:
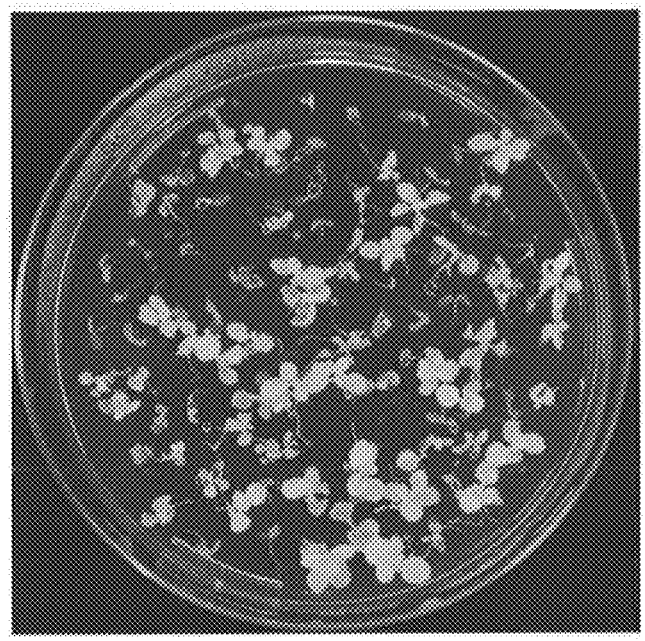
FIG. 2 is a photograph showing *Nicotrana benthanmiana* seedlings (2 weeks after transfer) selected with kanamycin resistance as an index after transfer of a complex of a carrier peptide and a nucleic acid.
Figures 1, 4:
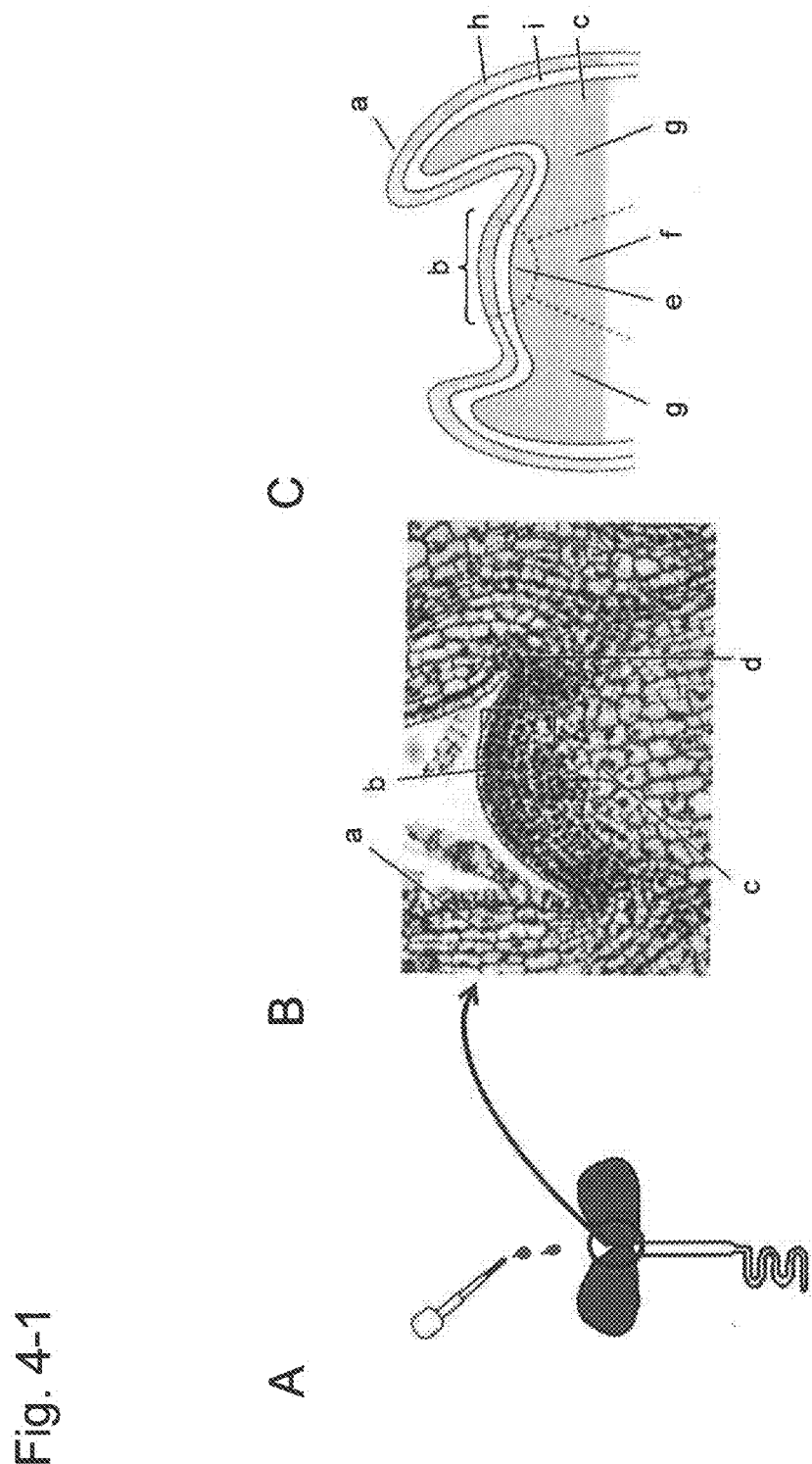
Figures 2, 4:
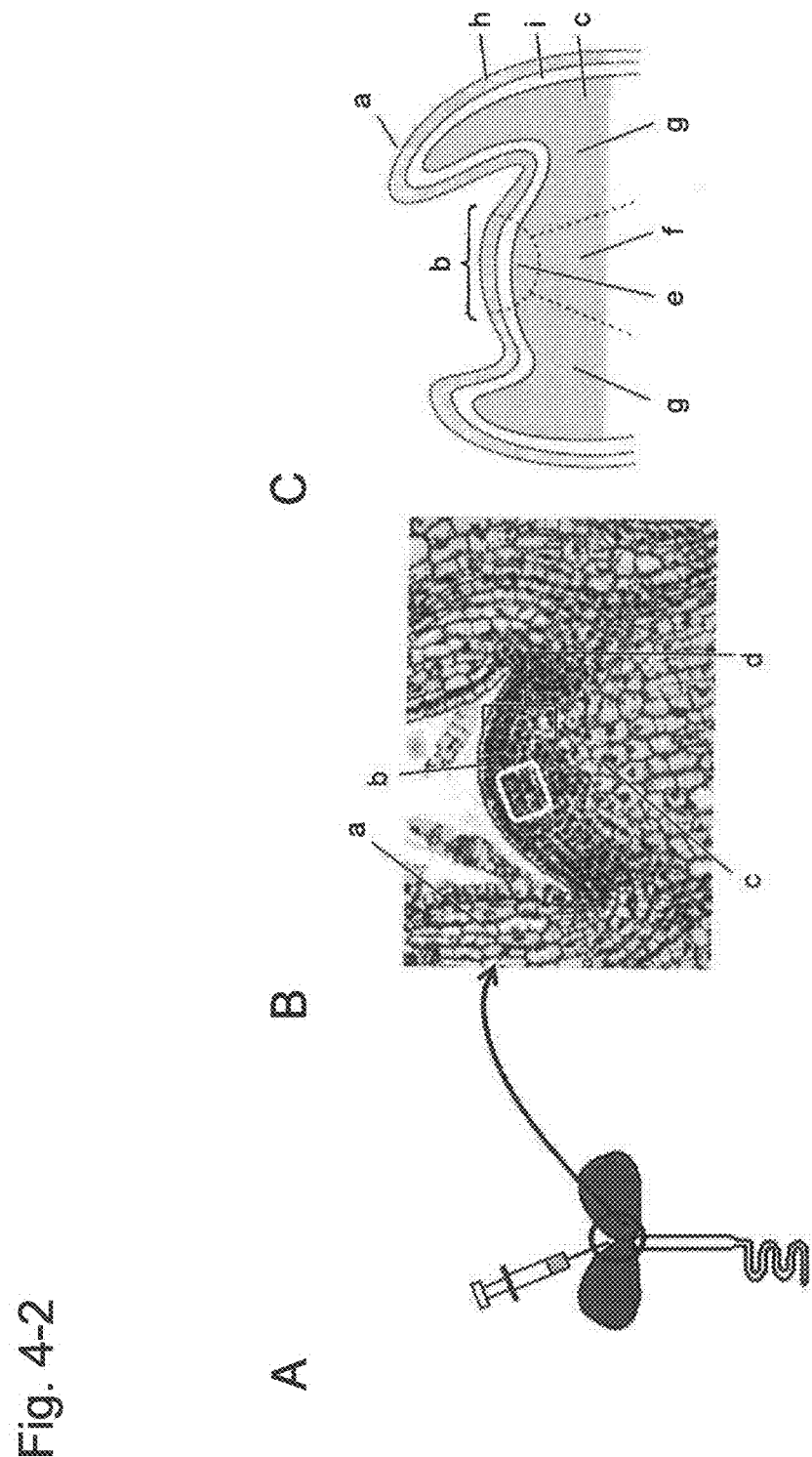

The step of contacting the complex with a cell of a meristem of the target plant can be carried out by a method known in the art and is not particularly limited. For example, the step of contacting can be carried out by permeating a solution of the complex of the carrier peptide and the nucleic acid into the cell of a meristem of the target plant and incubating it in an incubator under a constant light for 14 to 18 hours per day at a temperature of 20 to 35° C. Preferably, the solution of the complex can be efficiency permeated into the cell of the meristem by permeating the solution into a seedling of the target plant. The seedling is preferably a seedling 2 to 5 days after germination. The incubation time is preferably approximately 15 seconds to several minutes, more preferably approximately 1 minute. The solution of the complex of the carrier peptide and the nucleic acid may be added dropwise for transfer to the cell of a meristem of the target plant using a dropper or the like (FIG. 4-1) or may be directly injected to the cell of a meristem of the target plant using a syringe or the like (FIG. 4-2). The nucleic acid transfer according to the present invention is particularly excellent because the nucleic acid transfer is carried out in a relatively short time.

The step of allowing the meristem contacted with the complex to grow can be carried out by a method known in the art and is not particularly limited. For example, the seedling of the target plant into which the solution of the complex is permeated is transferred to a medium and allowed to grow under conditions suitable for the target plant.

The step of selecting a plant harboring the transferred nucleic acid can also be carried out by a method known in the art and is not particularly limited. The selection is appropriately performed by using the expression of a particular character brought about by the gene of interest or a marker gene, the disappearance of a particular character such as the deletion of a gene, or the like as an index, while recombinant tissues or recombinant individuals can be cultured by proliferation and redifferentiation according to routine methods. The gene of interest or the marker gene encompasses a nucleic acid encoding the gene. Transformants can be bred by collecting seed(s) from the plant obtained by redifferentiation, and using the obtained seed(s).

The plant harboring the transferred nucleic acid can be selected by using, for example, a nucleic acid containing a marker gene as the nucleic acid to be transferred. Any marker gene known in the art can be used without particular limitations. Examples thereof include drug resistance genes (e.g., kanamycin resistance gene, ampicillin resistance gene, and puromycin resistance gene), thymidine kinase gene, diphtheria toxin gene, green fluorescent protein (GFP) gene, and β glucuronidase (GUS) gene.

For example, a nucleic acid comprising a drug resistance gene in addition to the gene of interest to be transferred is used to form a complex with the carrier peptide. In the case of contacting this complex with a meristem to transfer the nucleic acid to the genome, a plant individual harboring the transferred nucleic acid in the genome can be selected by growing a tissue, which is yielded by the growing of the meristem, with being contacted with the corresponding drug so that only a plant individual having the drug resistance survives. In the case of contacting the complex with a shoot apical meristem to transfer the nucleic acid, growth is performed while the shoot apex is contacted with the drug. A surviving individual can be selected as a plant individual having the drug resistance, i.e., a plant individual harboring the transferred nucleic acid in the genome.

When the plant to be transformed is a seed plant, a seed harboring the transferred nucleic acid can be obtained by allowing the selected plant to further grow and collecting the seed. It is preferred that the further growth of the selected plant should be carried out by transplanting the plant to culture soil. In this context, the term "collect" has the same meaning as that of "harvest" used in the agricultural or horticultural field. Thus, the term "collect" widely includes not only the isolation of the seed itself but the recovery of a plant individual containing a seed from a growing region. By using the seed thus obtained, tissue culture is not needed and therefore permits stable collection of transformed plants. Once such a transformed plant is prepared, the lineage of the transformed plant can be maintained according to a usual breeding method for the plant species.

Hereinafter, the present invention will be described further specifically with reference to Examples. However, the present invention is not intended to be limited by these Examples.

Example 1

Synthesis of Carrier Peptide

As a carrier peptide comprising a cell-penetrating sequence and a polycation sequence, (KH)$_9$—BP100 (khkhkhkhkhkhkhkhkhKKLFKKILKYL (SEQ ID NO: 30), theoretical pI/Mw: 10.81/3809.71 Da) was synthesized by use of standard 9-fluorenylmethoxycarbonyl (Fmoc) solid-phase peptide synthesis (G. B. Fields and R. L. Noble, Int J Pept Protein Res 35 (3), 161 (1990)).

In the sequence, the amino acid sequence indicated by the lower-case letters refers to the polycation sequence. The polypeptide was purified by use of high-performance liquid chromatography (HPLC). Then, the molecular weight was confirmed by matrix-assisted laser desorption/ionization time-of-flight (MALDI-TOF) mass spectrometry.

In the same way as above, each of a carrier peptide comprising a polycation sequence and a chloroplast transit sequence (khkhkhkhkhkhkhkhkhMAMQAMFAFQYLLVM (SEQ ID NO: 33)), and a carrier peptide comprising a mitochondrial transit sequence and a polycation sequence (MLSLRQSIRFFKkhkhkhkhkhkhkhkhkh (SEQ ID NO: 34)) was synthesized.

Example 2

Preparation of Carrier Peptide-DNA Complex pBI121 (accession No. AF485783), which is a plasmid containing a kanamycin resistance gene for expression in plants, was linearized (14 Kb) by Inverse PCR and transferred as a foreign nucleic acid. The peptide-DNA complex was prepared by mixing the DNA (1 μg/μL) and the carrier peptide (KH)$_9$(SEQ ID NO: 22)-BP100 (1 μg/μL) synthesized in Example 1 at a ratio of 3:1 in a deionized water solution at room temperature. The N/P ratio was adjusted to 0.5. In this context, the N/P ratio refers to the number of an amine group derived from the carrier peptide/the number of a phosphate group derived from the DNA.

Example 3

Transformation—(1)

*Nicotiana benthamiana*, which is tobacco for research, was used as a plant to be transformed. The growth was performed in a phytotron whose inside temperature was set to 30° C., and the light environment was set to a continuous light. The germination was performed on an MS agar medium having half the normal concentration (0.5×MS medium, pH=5.7, containing no sucrose and vitamins). The sterile inoculation of *Nicotiana benthamiana* was carried out by treating the seeds with 70% EtOH, then sterilizing the seeds with 10% bleach for 30 minutes, then rinsing the seeds with sterile water three times, and inoculating the seeds to the medium.

8 μL of the peptide-DNA complex prepared in Example 2 was diluted (in a 1.5 mL, tube) with 192 μL of sterile water, and seedlings (50 individuals) 3 days after the germination of *Nicotiana benthamiana* were dipped in the diluted solution. The tube containing them was placed in a 50 mL syringe and kept for 1 minute in a state where the pressure was reduced to 0.5 atm. The seedlings thus treated with the peptide-DNA complex were transferred to a 0.5×MS medium and allowed to grow under the conditions described above.

The selection with an antibiotic was performed from 3 days after the treatment with the peptide-DNA complex. The concentration of kanamycin was adjusted to 25 mg/L with a sterilized 10% glycerin solution. This kanamycin solution was added dropwise in an amount of 2 μL to each shoot apex. This treatment was performed 4 times at 3- to 7-day intervals. Individuals surviving 2 weeks after the treatment were selected as individuals having kanamycin resistance. Approximately 40% antibiotic-resistant individuals were obtained by this selection (FIG. 2).

Figure 3:
FIG. 3 is a photograph showing results of electrophoresis of a kanamycin resistance gene amplified by PCR.

These antibiotic-resistant individuals were transplanted to culture soil and allowed to grow. Then, genomic DNA was extracted from the 7th true leaf to confirm that the foreign nucleic acid was inserted in the genome. The seedlings after the nucleic acid transfer were very young individuals 3 days after the germination. Since the 7th leaf is absent at this time, this leaf is considered to be derived from a shoot apical meristem after the nucleic acid transfer. The confirmation of the insertion was performed by amplifying the kanamycin resistance gene from the prepared genomic DNA by PCR using kanamycin resistance gene-specific primers. As a result, the resistance gene was able to be confirmed (FIG. 3). The numbers in the electrophoresis photograph of FIG. 3 represent the numbers of the kanamycin-resistant individuals. For Nos. 15 and 20, dark bands can be confirmed at the same position as that of PC (PCR product obtained with the gene used in the transfer as a template). In the case of using wild type-derived genomic DNA as a template, the same image as that of No. 18 was obtained. The transformation efficiency was 1.33%.

Example 4

Preparation of Carrier Peptide-DNA Complex—(2)

pUC19 and pCR2.1 (accession Nos. L09137 and 222717), which are plasmids containing a fluorescent protein GFPs65t and a spectinomycin resistance gene SPECr for expression in plants, were linearized (2.7 Kb and 4.1 Kb) by Inverse PCR and transferred as a foreign nucleic acid. The peptide-DNA complex was prepared by mixing the DNA (I µg/µL), the carrier peptides (1 µg/µL) of SEQ ID NO: 33 and SEQ ID NO: 34 synthesized in Example 1, and a peptide BP-100 (1 µg/µL) comprising a cell membrane-penetrating sequence at a ratio of 3:1:1 in a deionized water solution at room temperature. The N/P ratio was adjusted to 0.5.

Example 5

Transfer to Nicotiana tabacum Mitochondrion

Nicotiana tabacum of the family Solanaceae, which is general tobacco, was used as a plant to be transformed. The transformation method employed the same approach as in Example 3 except that spectinomycin was used instead of kanamycin as the antibiotic for use in selection.

The results are shown in FIG. 5. PCR was performed using a primer pair consisting of #1 (acaggtttagttgcctgtacc; SEQ ID NO: 35) complementary to the sequence on the mitochondrial genome and #2 (gaaaaattctatagaaacttctct-caattagttaatatttacttattattaatatttttaatta; SEQ ID NO: 36) complementary to a portion of the foreign nucleic acid (FIG. 5A) to confirm the transfer of the foreign nucleic acid to the mitochondrial genomic DNA. As a result, the transformant (T) was able to be confirmed to harbor the transferred 2.7 Kb gene of interest (FIG. 5B). On the other hand, no amplified band was able to be confirmed in a control (C) that had not been transformed.

Example 6

Transfer to Arabidopsis thaliana Chloroplast

Arabidopsis thaliana of the family Brassicaceae, which is a model plant, was used as a plant to be transformed. The transformation method employed the same approach as in Example 3 except that spectinomycin was used instead of kanamycin as the antibiotic for use in selection, to transfer the foreign nucleic acid of interest to the chloroplast genomic DNA.

Figure 6:
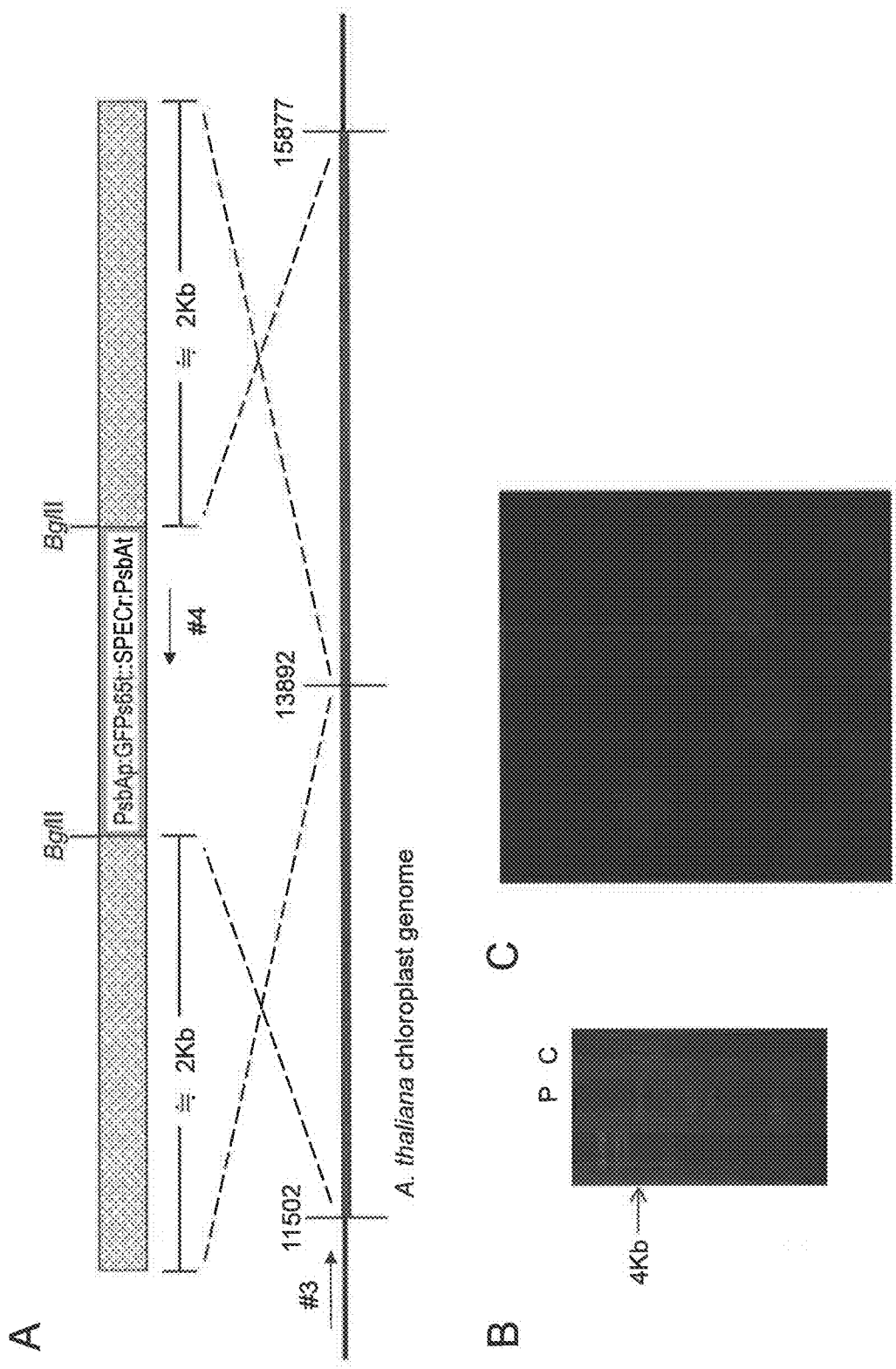
FIG. 6 is a diagram showing the transfer of a foreign nucleic acid of interest to the *Arabidopsis thaliana* chloroplast genome by the transformation method of the present invention.

The results are shown in FIG. 6. PCR was performed using a primer pair consisting of #3 (gttaccatgagtattgtcctg; SEQ ID NO: 37) complementary to the sequence on the chloroplast genome and #4 (tagctaattgagagaagtttctatag; SEQ ID NO: 38) complementary to a portion of the foreign nucleic acid (FIG. 6A) to confirm the transfer of the foreign nucleic acid to the chloroplast DNA. As a result, the transformant (P) was able to be confirmed to harbor the transferred 4.1 Kb gene of interest (FIG. 6B). On the other hand, no amplified band was able to be confirmed in a control (C) that had not been transformed. Furthermore, green light emission based on the expression of GFP was able to be observed in the chloroplast (FIG. 6C).

INDUSTRIAL APPLICABILITY

According to the present invention, various plant species can be easily exploited in matter production techniques, and novel plant species capable of producing bio-substances such as bioplastics or biofuels from carbon dioxide can be created. According to the present invention, there is the possibility that the construction of new biotechnology-based industry and the construction of low-carbon society can be achieved at the same time by substituting a wide range of matter production including not only bio-substances but also medical proteins, foods, and energy substances with a novel matter production technique exploiting plants and carbon dioxide.

All publications, patents, and patent applications cited herein are incorporated herein by reference in their entirety.

The invention claimed is:

1. A method for transforming a target plant, comprising the steps of:
   a) contacting a carrier peptide comprising a cell-penetrating sequence and a polycation sequence with a nucleic acid to form a complex;
   b) contacting the obtained complex with a cell of a meristem of the target plant to transfer the nucleic acid to the genome;
   c) allowing the meristem to grow; and
   d) selecting a plant harboring the transferred nucleic acid, wherein the carrier peptide comprises:
   (i) a cell-penetrating sequence selected from the group consisting of each of SEQ ID NOs:1-20, MPG, and Pep-1; and
   (ii) a polycationic sequence selected from the group consisting of a continuous series of 5 or more and 20 or less lysine (K) residues of SEQ ID NO: 39, a continuous series of 5 or more and 20 or less arginine (R) residues of SEQ ID NO: 40, a continuous series of 5 or more and 20 or less histidine (H) residues of SEQ ID NO: 41, 3 to 20 repeat sequences of KH of SEQ ID NO: 42, and 3 to 20 repeat sequences of RH of SEQ ID NO: 43,
   wherein the ratio of the number of amine groups in the carrier peptide and the number of phosphate groups in the nucleic acid (N/P ratio) is 0.2 or more and no more than 2.

2. The method according to claim 1, wherein the cell-penetrating sequence is BP100.

3. The method according to claim 1, wherein the polycation sequence is a sequence of 3 to 20 KH repeats of SEQ ID NO: 42.

4. The method according to claim 1, wherein the nucleic acid comprises a marker gene.

5. The method according to claim 1, wherein the plant is a seed plant, wherein the method further comprises a step of allowing the plant selected in the step d) to grow to collect a seed.

6. The method according to claim 1, wherein the meristem is a shoot apical meristem.

7. A method for transferring a nucleic acid to the genome of a target plant, comprising the steps of:
   a) contacting a carrier peptide comprising a cell-penetrating sequence and a polycation sequence with the nucleic acid to form a complex; and
   b) contacting the obtained complex with a cell of a meristem of the target plant to transfer the nucleic acid to the genome,
   wherein the carrier peptide comprises:
   (i) a cell-penetrating sequence selected from the group consisting of each of SEQ ID NOs:1-20, MPG, and Pep-1; and
   (ii) a polycationic sequence selected from the group consisting of a continuous series of 5 or more and 20 or less lysine (K) residues of SEQ ID NO: 39, a continuous series of 5 or more and 20 or less arginine (R) residues of SEQ ID NO: 40, a continuous series of 5 or more and 20 or less histidine (H) residues of SEQ ID NO: 41, 3 to 20 repeat sequences of KH of SEQ ID NO: 42, and 3 to 20 repeat sequences of RH of SEQ ID NO: 43,
   wherein the ratio of the number of amine groups in the carrier peptide and the number of phosphate groups in the nucleic acid (N/P ratio) is 0.2 or more and no more than 2.

8. The method according to claim 7, wherein the cell-penetrating sequence is BP100.

9. The method according to claim 7, wherein the polycation sequence is a sequence of 3 to 20 KH repeats of SEQ ID NO: 42.

10. The method according to claim 7, wherein the meristem is a shoot apical meristem.

* * * * *

SEQUENCE LISTING

```
<160> NUMBER OF SEQ ID NOS: 55

<210> SEQ ID NO 1
<211> LENGTH: 11
<212> TYPE: PRT
<213> ORGANISM: Artificial
<220> FEATURE:
<223> OTHER INFORMATION: Synthetic

<400> SEQUENCE: 1

Lys Lys Leu Phe Lys Lys Ile Leu Lys Tyr Leu
1               5                   10
```

```
<210> SEQ ID NO 2
<211> LENGTH: 18
<212> TYPE: PRT
<213> ORGANISM: Artificial
<220> FEATURE:
<223> OTHER INFORMATION: Synthetic

<400> SEQUENCE: 2

Arg Lys Lys Arg Arg Gln Arg Arg Arg Lys Lys Arg Arg Gln Arg
1               5                   10                  15

Arg Arg

<210> SEQ ID NO 3
<211> LENGTH: 9
<212> TYPE: PRT
<213> ORGANISM: Artificial
<220> FEATURE:
<223> OTHER INFORMATION: Synthetic

<400> SEQUENCE: 3

Arg Lys Lys Arg Arg Gln Arg Arg Arg
1               5

<210> SEQ ID NO 4
<211> LENGTH: 12
<212> TYPE: PRT
<213> ORGANISM: Artificial
<220> FEATURE:
<223> OTHER INFORMATION: Synthetic

<400> SEQUENCE: 4

Pro Leu Ser Ser Ile Phe Ser Arg Ile Gly Asp Pro
1               5                   10

<210> SEQ ID NO 5
<211> LENGTH: 12
<212> TYPE: PRT
<213> ORGANISM: Artificial
<220> FEATURE:
<223> OTHER INFORMATION: Synthetic

<400> SEQUENCE: 5

Pro Ile Ser Ser Ile Phe Ser Arg Thr Gly Asp Pro
1               5                   10

<210> SEQ ID NO 6
<211> LENGTH: 12
<212> TYPE: PRT
<213> ORGANISM: Artificial
<220> FEATURE:
<223> OTHER INFORMATION: Synthetic

<400> SEQUENCE: 6

Ala Ile Ser Ser Ile Leu Ser Lys Thr Gly Asp Pro
1               5                   10

<210> SEQ ID NO 7
<211> LENGTH: 12
<212> TYPE: PRT
<213> ORGANISM: Artificial
<220> FEATURE:
<223> OTHER INFORMATION: Synthetic

<400> SEQUENCE: 7

Pro Ile Leu Ser Ile Phe Ser Lys Ile Gly Asp Leu
```

```
1               5                   10

<210> SEQ ID NO 8
<211> LENGTH: 12
<212> TYPE: PRT
<213> ORGANISM: Artificial
<220> FEATURE:
<223> OTHER INFORMATION: Synthetic

<400> SEQUENCE: 8

Pro Leu Ser Ser Ile Phe Ser Lys Ile Gly Asp Pro
1               5                   10

<210> SEQ ID NO 9
<211> LENGTH: 12
<212> TYPE: PRT
<213> ORGANISM: Artificial
<220> FEATURE:
<223> OTHER INFORMATION: Synthetic

<400> SEQUENCE: 9

Pro Leu Ser Ser Ile Phe Ser His Ile Gly Asp Pro
1               5                   10

<210> SEQ ID NO 10
<211> LENGTH: 12
<212> TYPE: PRT
<213> ORGANISM: Artificial
<220> FEATURE:
<223> OTHER INFORMATION: Synthetic

<400> SEQUENCE: 10

Pro Leu Ser Ser Ile Phe Ser Ser Ile Gly Asp Pro
1               5                   10

<210> SEQ ID NO 11
<211> LENGTH: 16
<212> TYPE: PRT
<213> ORGANISM: Artificial
<220> FEATURE:
<223> OTHER INFORMATION: Synthetic

<400> SEQUENCE: 11

Arg Gln Ile Lys Ile Trp Phe Gln Asn Arg Arg Met Lys Trp Lys Lys
1               5                   10                  15

<210> SEQ ID NO 12
<211> LENGTH: 34
<212> TYPE: PRT
<213> ORGANISM: Artificial
<220> FEATURE:
<223> OTHER INFORMATION: Synthetic

<400> SEQUENCE: 12

Asp Ala Ala Thr Ala Thr Arg Gly Arg Ser Ala Ala Ser Arg Pro Thr
1               5                   10                  15

Glu Arg Pro Arg Ala Pro Ala Arg Ser Ala Ser Arg Pro Arg Arg Pro
                20                  25                  30

Val Asp

<210> SEQ ID NO 13
<211> LENGTH: 16
<212> TYPE: PRT
<213> ORGANISM: Artificial
<220> FEATURE:
<223> OTHER INFORMATION: Synthetic
```

```
<400> SEQUENCE: 13

Ala Ala Val Ala Leu Leu Pro Ala Val Leu Leu Ala Leu Leu Ala Pro
1               5                   10                  15

<210> SEQ ID NO 14
<211> LENGTH: 12
<212> TYPE: PRT
<213> ORGANISM: Artificial
<220> FEATURE:
<223> OTHER INFORMATION: Synthetic

<400> SEQUENCE: 14

Ala Ala Val Leu Leu Pro Val Leu Leu Ala Ala Pro
1               5                   10

<210> SEQ ID NO 15
<211> LENGTH: 15
<212> TYPE: PRT
<213> ORGANISM: Artificial
<220> FEATURE:
<223> OTHER INFORMATION: Synthetic

<400> SEQUENCE: 15

Val Thr Val Leu Ala Leu Gly Ala Leu Ala Gly Val Gly Val Gly
1               5                   10                  15

<210> SEQ ID NO 16
<211> LENGTH: 17
<212> TYPE: PRT
<213> ORGANISM: Artificial
<220> FEATURE:
<223> OTHER INFORMATION: Synthetic

<400> SEQUENCE: 16

Gly Ala Leu Phe Leu Gly Trp Leu Gly Ala Ala Gly Ser Thr Met Gly
1               5                   10                  15

Ala

<210> SEQ ID NO 17
<211> LENGTH: 17
<212> TYPE: PRT
<213> ORGANISM: Artificial
<220> FEATURE:
<223> OTHER INFORMATION: Synthetic

<400> SEQUENCE: 17

Met Gly Leu Gly Leu His Leu Leu Val Leu Ala Ala Ala Leu Gln Gly
1               5                   10                  15

Ala

<210> SEQ ID NO 18
<211> LENGTH: 24
<212> TYPE: PRT
<213> ORGANISM: Artificial
<220> FEATURE:
<223> OTHER INFORMATION: Synthetic

<400> SEQUENCE: 18

Leu Gly Thr Tyr Thr Gln Asp Phe Asn Lys Phe His Thr Phe Pro Gln
1               5                   10                  15

Thr Ala Ile Gly Val Gly Ala Pro
            20
```

```
<210> SEQ ID NO 19
<211> LENGTH: 26
<212> TYPE: PRT
<213> ORGANISM: Artificial
<220> FEATURE:
<223> OTHER INFORMATION: Synthetic

<400> SEQUENCE: 19

Gly Trp Thr Leu Asn Ser Ala Gly Tyr Leu Leu Lys Ile Asn Leu Lys
1               5                   10                  15

Ala Leu Ala Ala Leu Ala Lys Lys Ile Leu
            20                  25

<210> SEQ ID NO 20
<211> LENGTH: 18
<212> TYPE: PRT
<213> ORGANISM: Artificial
<220> FEATURE:
<223> OTHER INFORMATION: Synthetic

<400> SEQUENCE: 20

Lys Leu Ala Leu Lys Leu Ala Leu Ala Leu Lys Ala Ala Leu Lys
1               5                   10                  15

Leu Ala

<210> SEQ ID NO 21
<211> LENGTH: 6
<212> TYPE: PRT
<213> ORGANISM: Artificial
<220> FEATURE:
<223> OTHER INFORMATION: Synthetic

<400> SEQUENCE: 21

Arg Arg Arg Arg Arg Arg
1               5

<210> SEQ ID NO 22
<211> LENGTH: 18
<212> TYPE: PRT
<213> ORGANISM: Artificial
<220> FEATURE:
<223> OTHER INFORMATION: Synthetic

<400> SEQUENCE: 22

Lys His Lys His Lys His Lys His Lys His Lys His Lys His Lys His
1               5                   10                  15

Lys His

<210> SEQ ID NO 23
<211> LENGTH: 32
<212> TYPE: PRT
<213> ORGANISM: Artificial
<220> FEATURE:
<223> OTHER INFORMATION: Synthetic

<400> SEQUENCE: 23

Met Ala Met Ala Met Arg Ser Thr Phe Ala Ala Arg Val Gly Ala Lys
1               5                   10                  15

Pro Ala Val Arg Gly Ala Arg Pro Ala Ser Arg Met Ser Cys Met Ala
            20                  25                  30

<210> SEQ ID NO 24
<211> LENGTH: 32
<212> TYPE: PRT
<213> ORGANISM: Artificial
```

```
<220> FEATURE:
<223> OTHER INFORMATION: Synthetic

<400> SEQUENCE: 24

Met Gln Val Thr Met Lys Ser Ala Val Ser Gly Gln Arg Val Gly
1               5                   10                  15

Gly Ala Arg Val Ala Thr Arg Ser Val Arg Arg Ala Gln Leu Gln Val
            20                  25                  30

<210> SEQ ID NO 25
<211> LENGTH: 74
<212> TYPE: PRT
<213> ORGANISM: Artificial
<220> FEATURE:
<223> OTHER INFORMATION: Synthetic

<400> SEQUENCE: 25

Met Ala Thr Met Val Ala Gly Ile Ser Leu Arg Gly Pro Val Met Ser
1               5                   10                  15

Ser His Arg Thr Phe Ser Val Thr Lys Arg Ala Ser Leu Pro Gln Ser
            20                  25                  30

Lys Leu Ser Ser Glu Leu Ser Phe Val Thr Ser Gln Leu Ser Gly Leu
        35                  40                  45

Lys Ile Ser Ser Thr His Phe Ile Ser Ser Ala Pro Leu Ser Val
    50                  55                  60

Pro Phe Lys Pro Ser Leu Gln Pro Val Ala
65                  70

<210> SEQ ID NO 26
<211> LENGTH: 41
<212> TYPE: PRT
<213> ORGANISM: Artificial
<220> FEATURE:
<223> OTHER INFORMATION: Synthetic

<400> SEQUENCE: 26

Met Ala Ala Leu Gln Ser Ser Phe Ala Gly Leu Ser Thr Ser Phe Phe
1               5                   10                  15

Gly Gln Arg Phe Ser Pro Pro Leu Ser Leu Pro Pro Leu Val Lys Ser
            20                  25                  30

Thr Glu Gly Pro Cys Leu Ile Gln Ala
        35                  40

<210> SEQ ID NO 27
<211> LENGTH: 51
<212> TYPE: PRT
<213> ORGANISM: Artificial
<220> FEATURE:
<223> OTHER INFORMATION: Synthetic

<400> SEQUENCE: 27

Met Ala Val Ser Phe Ser Leu Val Gly Ala Phe Lys Gly Leu Ser Leu
1               5                   10                  15

Ala Ser Ser Ser Ser Phe Leu Lys Gly Asp Phe Gly Ala Ala Phe Pro
            20                  25                  30

Val Ala Pro Lys Phe Ser Val Ser Phe Pro Leu Lys Ser Pro Leu Thr
        35                  40                  45

Ile Glu Ser
    50

<210> SEQ ID NO 28
```

```
<211> LENGTH: 57
<212> TYPE: PRT
<213> ORGANISM: Artificial
<220> FEATURE:
<223> OTHER INFORMATION: Synthetic

<400> SEQUENCE: 28

Met Ala Ser Ser Val Leu Ser Ser Ala Ala Val Ala Thr Arg Ser Asn
1               5                   10                  15

Val Ala Gln Ala Asn Met Val Ala Pro Phe Thr Gly Leu Lys Ser Ala
            20                  25                  30

Ala Ser Phe Pro Val Ser Arg Lys Gln Asn Leu Asp Ile Thr Ser Ile
        35                  40                  45

Ala Ser Asn Gly Gly Arg Val Gln Cys
    50                  55

<210> SEQ ID NO 29
<211> LENGTH: 39
<212> TYPE: PRT
<213> ORGANISM: Artificial
<220> FEATURE:
<223> OTHER INFORMATION: Synthetic

<400> SEQUENCE: 29

Met Ala Ala Ser Thr Met Ala Leu Ser Ser Pro Ala Phe Ala Gly Lys
1               5                   10                  15

Ala Val Lys Leu Ser Pro Ala Ala Ser Glu Val Leu Gly Ser Gly Arg
            20                  25                  30

Val Thr Met Arg Lys Thr Val
        35

<210> SEQ ID NO 30
<211> LENGTH: 29
<212> TYPE: PRT
<213> ORGANISM: Artificial
<220> FEATURE:
<223> OTHER INFORMATION: Synthetic

<400> SEQUENCE: 30

Lys His Lys His Lys His Lys His Lys His Lys His Lys His Lys His
1               5                   10                  15

Lys His Lys Lys Leu Phe Lys Lys Ile Leu Lys Tyr Leu
            20                  25

<210> SEQ ID NO 31
<211> LENGTH: 12
<212> TYPE: PRT
<213> ORGANISM: Artificial
<220> FEATURE:
<223> OTHER INFORMATION: Synthetic

<400> SEQUENCE: 31

Met Leu Ser Leu Arg Gln Ser Ile Arg Phe Phe Lys
1               5                   10

<210> SEQ ID NO 32
<211> LENGTH: 15
<212> TYPE: PRT
<213> ORGANISM: Artificial
<220> FEATURE:
<223> OTHER INFORMATION: Synthetic

<400> SEQUENCE: 32

Met Ala Met Gln Ala Met Phe Ala Phe Gln Tyr Leu Leu Val Met
```

-continued

```
<210> SEQ ID NO 33
<211> LENGTH: 33
<212> TYPE: PRT
<213> ORGANISM: Artificial
<220> FEATURE:
<223> OTHER INFORMATION: Synthetic

<400> SEQUENCE: 33

Lys His Lys His Lys His Lys His Lys His Lys His Lys His Lys His
1               5                   10                  15

Lys His Met Ala Met Gln Ala Met Phe Ala Phe Gln Tyr Leu Leu Val
            20                  25                  30

Met

<210> SEQ ID NO 34
<211> LENGTH: 30
<212> TYPE: PRT
<213> ORGANISM: Artificial
<220> FEATURE:
<223> OTHER INFORMATION: Synthetic

<400> SEQUENCE: 34

Met Leu Ser Leu Arg Gln Ser Ile Arg Phe Phe Lys Lys His Lys His
1               5                   10                  15

Lys His Lys His Lys His Lys His Lys His Lys His Lys His
            20                  25                  30

<210> SEQ ID NO 35
<211> LENGTH: 21
<212> TYPE: DNA
<213> ORGANISM: Artificial
<220> FEATURE:
<223> OTHER INFORMATION: Primer

<400> SEQUENCE: 35
acaggtttag ttgcctgtac c                                              21

<210> SEQ ID NO 36
<211> LENGTH: 64
<212> TYPE: DNA
<213> ORGANISM: Artificial
<220> FEATURE:
<223> OTHER INFORMATION: Primer

<400> SEQUENCE: 36
gaaaaattct atagaaactt ctctcaatta gttaatattt acttattatt aatattttta   60
atta                                                                 64

<210> SEQ ID NO 37
<211> LENGTH: 21
<212> TYPE: DNA
<213> ORGANISM: Artificial
<220> FEATURE:
<223> OTHER INFORMATION: Primer

<400> SEQUENCE: 37
gttaccatga gtattgtcct g                                              21

<210> SEQ ID NO 38
<211> LENGTH: 26
<212> TYPE: DNA
<213> ORGANISM: Artificial
```

```
<220> FEATURE:
<223> OTHER INFORMATION: Primer

<400> SEQUENCE: 38
tagctaattg agagaagttt ctatag                                              26

<210> SEQ ID NO 39
<211> LENGTH: 20
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(20)
<223> OTHER INFORMATION: This sequence may encompass 5-20 residues

<400> SEQUENCE: 39

Lys Lys Lys Lys Lys Lys Lys Lys Lys Lys Lys Lys Lys Lys Lys Lys
1               5                   10                  15

Lys Lys Lys Lys
            20

<210> SEQ ID NO 40
<211> LENGTH: 20
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(20)
<223> OTHER INFORMATION: This sequence may encompass 5-20 residues

<400> SEQUENCE: 40

Arg Arg Arg Arg Arg Arg Arg Arg Arg Arg Arg Arg Arg Arg Arg Arg
1               5                   10                  15

Arg Arg Arg Arg
            20

<210> SEQ ID NO 41
<211> LENGTH: 20
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(20)
<223> OTHER INFORMATION: This sequence may encompass 5-20 residues

<400> SEQUENCE: 41

His His His His His His His His His His His His His His His His
1               5                   10                  15

His His His His
            20

<210> SEQ ID NO 42
<211> LENGTH: 40
<212> TYPE: PRT
<213> ORGANISM: Artificial
<220> FEATURE:
<223> OTHER INFORMATION: Synthetic polypeptide
<220> FEATURE:
<221> NAME/KEY: MISC_FEATURE
<222> LOCATION: (1)..(40)
<223> OTHER INFORMATION: This sequence may encompass 3-20 "Lys His"
      repeating units
```

<400> SEQUENCE: 42

Lys His Lys His Lys His Lys His Lys His Lys His Lys His Lys His
1               5                   10                  15

Lys His Lys His Lys His Lys His Lys His Lys His Lys His Lys His
                20                  25                  30

Lys His Lys His Lys His Lys His
        35                  40

<210> SEQ ID NO 43
<211> LENGTH: 40
<212> TYPE: PRT
<213> ORGANISM: Artificial
<220> FEATURE:
<223> OTHER INFORMATION: Synthetic polypeptide
<220> FEATURE:
<221> NAME/KEY: MISC_FEATURE
<222> LOCATION: (1)..(40)
<223> OTHER INFORMATION: This sequence may encompass 3-20 "Arg His"
      repeating units

<400> SEQUENCE: 43

Arg His Arg His Arg His Arg His Arg His Arg His Arg His Arg His
1               5                   10                  15

Arg His Arg His Arg His Arg His Arg His Arg His Arg His Arg His
                20                  25                  30

Arg His Arg His Arg His Arg His
        35                  40

<210> SEQ ID NO 44
<211> LENGTH: 7
<212> TYPE: PRT
<213> ORGANISM: Artificial
<220> FEATURE:
<223> OTHER INFORMATION: Synthetic peptide

<400> SEQUENCE: 44

Arg Arg Arg Arg Arg Arg Arg
1               5

<210> SEQ ID NO 45
<211> LENGTH: 30
<212> TYPE: PRT
<213> ORGANISM: Artificial
<220> FEATURE:
<223> OTHER INFORMATION: Synthetic polypeptide
<220> FEATURE:
<221> NAME/KEY: MISC_FEATURE
<222> LOCATION: (1)..(30)
<223> OTHER INFORMATION: This sequence may encompass 5-15 "Lys His"
      repeating units

<400> SEQUENCE: 45

Lys His Lys His Lys His Lys His Lys His Lys His Lys His Lys His
1               5                   10                  15

Lys His Lys His Lys His Lys His Lys His Lys His Lys His
                20                  25                  30

<210> SEQ ID NO 46
<211> LENGTH: 24
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE

```
<222> LOCATION: (1)..(24)
<223> OTHER INFORMATION: This sequence may encompass 7-12 "Lys His"
      repeating units

<400> SEQUENCE: 46

Lys His Lys His Lys His Lys His Lys His Lys His Lys His Lys His
1               5                   10                  15

Lys His Lys His Lys His Lys His
            20

<210> SEQ ID NO 47
<211> LENGTH: 15
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(15)
<223> OTHER INFORMATION: This sequence may encompass 5-15 residues

<400> SEQUENCE: 47

Arg Arg Arg Arg Arg Arg Arg Arg Arg Arg Arg Arg Arg Arg Arg
1               5                   10                  15

<210> SEQ ID NO 48
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(12)
<223> OTHER INFORMATION: This sequence may encompass 7-12 residues

<400> SEQUENCE: 48

Arg Arg Arg Arg Arg Arg Arg Arg Arg Arg Arg Arg
1               5                   10

<210> SEQ ID NO 49
<211> LENGTH: 20
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(20)
<223> OTHER INFORMATION: This sequence may encompass 3-20 residues

<400> SEQUENCE: 49

Lys Lys Lys Lys Lys Lys Lys Lys Lys Lys Lys Lys Lys Lys Lys Lys
1               5                   10                  15

Lys Lys Lys Lys
            20

<210> SEQ ID NO 50
<211> LENGTH: 15
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(15)
<223> OTHER INFORMATION: This sequence may encompass 5-15 residues

<400> SEQUENCE: 50
```

```
Lys Lys Lys Lys Lys Lys Lys Lys Lys Lys Lys Lys Lys Lys Lys
1               5                   10                  15

<210> SEQ ID NO 51
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(12)
<223> OTHER INFORMATION: This sequence may encompass 7-12 residues

<400> SEQUENCE: 51

Lys Lys Lys Lys Lys Lys Lys Lys Lys Lys Lys Lys
1               5                   10

<210> SEQ ID NO 52
<211> LENGTH: 20
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(20)
<223> OTHER INFORMATION: This sequence may encompass 3-20 residues

<400> SEQUENCE: 52

His His His His His His His His His His His His His His His His
1               5                   10                  15

His His His His
            20

<210> SEQ ID NO 53
<211> LENGTH: 15
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(15)
<223> OTHER INFORMATION: This sequence may encompass 5-15 residues

<400> SEQUENCE: 53

His His His His His His His His His His His His His His His
1               5                   10                  15

<210> SEQ ID NO 54
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(12)
<223> OTHER INFORMATION: This sequence may encompass 7-12 residues

<400> SEQUENCE: 54

His His His His His His His His His His His His
1               5                   10

<210> SEQ ID NO 55
<211> LENGTH: 20
<212> TYPE: PRT
```

```
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(20)
<223> OTHER INFORMATION: This sequence may encompass 3-20 residues

<400> SEQUENCE: 55

Arg Arg Arg Arg Arg Arg Arg Arg Arg Arg Arg Arg Arg Arg Arg
1               5                   10                  15

Arg Arg Arg Arg
            20
```